US012564315B2

(12) United States Patent
Lund et al.

(10) Patent No.: US 12,564,315 B2
(45) Date of Patent: Mar. 3, 2026

(54) SLIDING MOTION TRANSFER MEMBER FOR AN ENDOSCOPE

(71) Applicant: AMBU A/S, Ballerup (DK)

(72) Inventors: Jesper Grøndahl Lund, Værløse (DK); Tan Xian Wei, Air Itam (MY); Ilona Dillinger, Aindling (DE)

(73) Assignee: AMBU A/S, Ballerup (DK)

( * ) Notice: Subject to any disclaimer, the term of this patent is extended or adjusted under 35 U.S.C. 154(b) by 556 days.

(21) Appl. No.: 18/008,876

(22) PCT Filed: Jun. 2, 2021

(86) PCT No.: PCT/DK2021/050172
§ 371 (c)(1),
(2) Date: Dec. 7, 2022

(87) PCT Pub. No.: WO2021/249601
PCT Pub. Date: Dec. 16, 2021

(65) Prior Publication Data
US 2023/0233067 A1 Jul. 27, 2023

(30) Foreign Application Priority Data
Jun. 8, 2020 (DK) ........................... PA 2020 70360

(51) Int. Cl.
*A61B 1/00* (2006.01)
*A61B 1/005* (2006.01)
(52) U.S. Cl.
CPC .......... *A61B 1/0057* (2013.01); *A61B 1/0011* (2013.01); *A61B 1/00128* (2013.01)
(58) Field of Classification Search
None
See application file for complete search history.

(56) References Cited

U.S. PATENT DOCUMENTS

| | | | |
|---|---|---|---|
| 5,275,151 A | 1/1994 | Shockey et al. | |
| 5,569,157 A | 10/1996 | Nakazawa et al. | |
| | (Continued) | | |

FOREIGN PATENT DOCUMENTS

| | | | |
|---|---|---|---|
| CN | 106880332 A | 6/2017 | |
| EP | 0165718 A2 | 12/1985 | |
| | (Continued) | | |

OTHER PUBLICATIONS

Search report in Danish Patent Application No. PA 2020 70360, mailed Sep. 18, 2020, 8 pages.

(Continued)

*Primary Examiner* — Anh Tuan T Nguyen
*Assistant Examiner* — Rynae E Boler
(74) *Attorney, Agent, or Firm* — Faegre Drinker Biddle & Reath LLP

(57) ABSTRACT

A sliding motion transfer member (22) for the kinematic chain of an actuator mechanism of an endoscope. The sliding motion transfer member (22) has a proximal end and a distal end (21). The sliding motion transfer member (22) is adapted to receive motion activation input and to move in a sliding manner in response to the motion activation input, thereby transferring motion to an elongate motion transmission member (27) extending from the distal end (21) of the sliding motion transfer member (20). The sliding motion transfer member (22) includes a first passage (36) adapted for receiving a proximal section of the elongate motion transmission member (20) and an adhesive.

20 Claims, 9 Drawing Sheets

(56)                    References Cited

U.S. PATENT DOCUMENTS

| | | | |
|---|---|---|---|
| 5,762,067 A | 6/1998 | Dunham et al. | |
| 5,810,876 A | 9/1998 | Kelleher | |
| 9,089,263 B2 | 7/2015 | Maruyama | |
| 2001/0044570 A1 * | 11/2001 | Ouchi | A61B 1/018 |
| | | | 600/107 |
| 2005/0070764 A1 | 3/2005 | Nobis et al. | |
| 2013/0204096 A1 | 8/2013 | Ku et al. | |
| 2014/0114131 A1 * | 4/2014 | Sakai | A61B 1/0011 |
| | | | 600/182 |
| 2014/0200402 A1 | 7/2014 | Snoke et al. | |
| 2014/0243615 A1 | 8/2014 | Schaeffer et al. | |
| 2014/0336532 A1 | 11/2014 | Seguy | |
| 2014/0371534 A1 | 12/2014 | Okamoto | |
| 2015/0148598 A1 * | 5/2015 | Fukushima | A61B 1/00098 |
| | | | 600/109 |
| 2015/0366436 A1 * | 12/2015 | Iuel | A61M 25/0147 |
| | | | 600/149 |
| 2016/0089125 A1 * | 3/2016 | Morimoto | A61B 1/00098 |
| | | | 600/107 |
| 2016/0150946 A1 * | 6/2016 | Tsumaru | A61B 1/126 |
| | | | 600/107 |
| 2017/0215704 A1 * | 8/2017 | Tsumaru | A61B 1/00128 |
| 2017/0296388 A1 | 10/2017 | Gaynes et al. | |
| 2018/0028786 A1 | 2/2018 | Jungles | |
| 2018/0035870 A1 | 2/2018 | Okaniwa et al. | |
| 2018/0303315 A1 | 10/2018 | Matthison-Hansen | |
| 2018/0309908 A1 | 10/2018 | Matthison-Hansen et al. | |
| 2023/0148844 A1 | 5/2023 | Christensen et al. | |
| 2023/0157519 A1 | 5/2023 | Lund et al. | |
| 2023/0165436 A1 | 6/2023 | Lund et al. | |
| 2023/0172439 A1 | 6/2023 | Lund et al. | |

FOREIGN PATENT DOCUMENTS

| | | | | |
|---|---|---|---|---|
| EP | 3269292 A1 | 1/2018 | | |
| JP | H07148104 A | 6/1995 | | |
| JP | 2003305002 A | * 10/2003 | | A61B 1/00098 |
| JP | 2011050643 A | 3/2011 | | |
| WO | 2013099390 A1 | 7/2013 | | |

OTHER PUBLICATIONS

International Search Report and Written Opinion received for PCT Patent Application No. PCT/DK2021/050172, Issued on Aug. 25, 2021, 8 pages.

* cited by examiner

SLIDING MOTION TRANSFER MEMBER FOR AN ENDOSCOPE

CROSS REFERENCE TO RELATED APPLICATIONS

This application is a National Phase entry under 35 U.S.C. § 371 of International Application No. PCT/DK2021/050172, filed Jun. 2, 2021, which claims the benefit of and priority from Danish Patent Application No. PA 2020 70360, filed Jun. 8, 2020; said applications are incorporated by reference herein in their entirety.

TECHNICAL FIELD

The present disclosure relates to endoscopes, more specifically to a sliding motion transfer member for the kinematic chain of an actuator mechanism of an endoscope, in particular, but not exclusively, a disposable endoscope. Moreover, the disclosure relates to a method of fastening a motion transmission member to the sliding motion transfer member.

BACKGROUND

Endoscopes typically comprises a handle gripped by an operator and a flexible insertion tube terminated at the distal end in a highly bendable, e.g. articulated, bending section, controllable by the operator. Thus, the controllable bending section is normally an articulated section at the distal tip of the insertion tube that can be controlled by the operator via control knobs arranged on the handle, allowing the operator to advance the distal tip of the endoscope to a desired location by means of a series of actions involving inter alia bending the bending section in a desired direction, advancing the insertion tube and turning the insertion tube by turning the handle which is rigidly connected thereto.

When the distal tip of the insertion tube has reached the point of interest there may be a need for action, rather than visual inspection only. This may involve the deployment of a built-in tool or the like. Though, not limited to the use therein, the outset of the present disclosure is duodenoscopes.

A duodenoscope is a flexible endoscope configured to access a patient's duodenum from the stomach via the patient's mouth. When the tip of the insertion tube is positioned in the duodenum there is a need to guide a tool radially from the tip, e.g. towards the biliary ducts in the wall of the duodenum. For that purpose, the camera and the exit of a working channel of a duodenoscope is, unlike many other types of endoscopes, not positioned at the end surface of the distal tip. Moreover, in order to accommodate different needs for guiding the tool the exit port of the working channel is provided with a lever that is operated by pulling and pushing a wire connected to an operating member at the endoscope handle. The lever or tool lift is also known as an Albarran mechanism from the original inventor. An example of such an endoscope is known from U.S. Pat. No. 9,089,263, incorporated herein by reference. The lever of U.S. Pat. No. 9,089,269 thus constitutes a built-in tool especially adapted to guide a secondary tool. The tool is connected to the operating lever via a suitable kinematic chain allowing motion of the operating member to be transmitted to the tool.

U.S. Pat. No. 9,089,263 does not go into detail with this kinematic chain but only briefly describes the use of a wire connected at the proximal end to the operating member via an arm referred to as a wire coupling member. From the sparse details given in U.S. Pat. No. 9,089,263, it is hard to see how an accurate and reliable motion transmission can be achieved.

Another example of an endoscope with a built-in tool operated via a rather complex kinematic chain is found in WO2016/188542.

BRIEF DESCRIPTION OF THE DISCLOSURE

Based on the above it is the object of the present disclosure to provide an accurate and reliable motion transmission between the operating member at the proximal end of a, preferably disposable, endoscope, i.e. at the handle and a tool at the distal end, i.e. at the tip of the insertion tube. This, while at the same time making the constituent parts, and the assembly thereof cost efficient.

According to a first aspect of the disclosure, this object is achieved by a sliding motion transfer member for the kinematic chain of an actuator mechanism of an endoscope, said sliding motion transfer member having a proximal end and a distal end, the slider being adapted to receive motion activation input and to move in a sliding manner in response to said motion activation input, thereby transferring motion to an elongate motion transmission member extending from the distal end of the sliding motion transfer member, said sliding motion transfer member comprising a first passage adapted for receiving a proximal section of said elongate motion transmission member and an adhesive so as to secure the proximal section of said elongate motion transmission member with respect to said sliding motion transfer member.

By using a sliding motion transfer member of this kind, a precise conversion of the rotary motion of the operating member to a linear motion may be achieved in the kinematic chain, without play or wobble. This is partly because the sliding motion transfer member may be guided in a precise linear motion, e.g. by suitable guiding part in or integrated in the housing. At the same time the sliding member provides a firm and precise connection between the operating member and the elongate motion transmission member.

According to a second aspect of the disclosure, the object is achieved by an endoscope comprising a sliding motion transfer member according to the first aspect of the disclosure.

According to a third aspect of the disclosure, the object is achieved by a method of fastening an elongate motion transmission member to a sliding motion transfer member in of an endoscope, said method comprising providing a sliding motion transfer member according to the first object of the disclosure, placing said elongate motion transmission member in said first passage, introducing an adhesive into said passage, and allowing said adhesive to bond to said elongate motion transmission member in said first passage. The use of an adhesive adhering to the elongate motion transmission member allows the positive or form locking connection between the elongate motion transmission member to be established, in turn securing the elongate motion transmission member, even if the sliding motion transfer member itself is made in a low friction or non-stick material to which the adhesive will not or only weakly adhere.

According to a fourth aspect of the disclosure, the object is achieved by a system comprising an endoscope according to the third aspect and a display unit connectable to said endoscope, thereby providing a complete and versatile medical system.

According to a first preferred embodiment of the first aspect of the disclosure further comprising a second passage adapted to receive a screw in a manner allowing said screw to engage said proximal section of said elongate motion transmission member, said second passage being arranged in a cross-wise direction with respect to said first passage. Using a screw may further strengthen the fastening of the elongate motion transmission member in the sliding motion transfer member. This is especially important when, as preferred, the sliding motion transfer member is made of a low friction material.

According to another preferred embodiment of the first aspect of the disclosure, a first adhesive inlet passage is arranged in a cross-wise direction with respect to said first passage and in fluid communication with respect to said first passage. This allows adhesive to be easily poured into the passage during assembly, flow along the proximal section of the motion transmission member and adhere thereto to form the positive connection.

According to a further preferred embodiment of the first aspect of the disclosure, a second adhesive inlet passage is arranged in a cross-wise direction with respect to said first passage and in fluid communication with respect to said first passage. This in a similar manner allows adhesive to be easily poured into the passage during assembly, flow along a support member for proximal section of the motion transmission member and adhere thereto.

According to a yet a further preferred embodiment, the first passage has a varying cross-sectional area. This allows the adhesive to set in a shape corresponding to the varying cross-sectional area, thereby providing the form locking or positive connection.

According to yet another preferred embodiment, the cross-sectional area increases from said second passage towards the proximal end of the sliding motion transfer member. This facilitates the flow from the inlet towards, the preferably open proximal end of the passage.

According to another preferred embodiment, the first passage is frusto-conical, which from a manufacturing point of view is advantageous.

BRIEF DESCRIPTION OF THE DRAWINGS

The disclosure will now be made in greater detail based on non-limiting exemplary embodiments and with reference to the drawing, on which.

DETAILED DESCRIPTION

Figure 1:
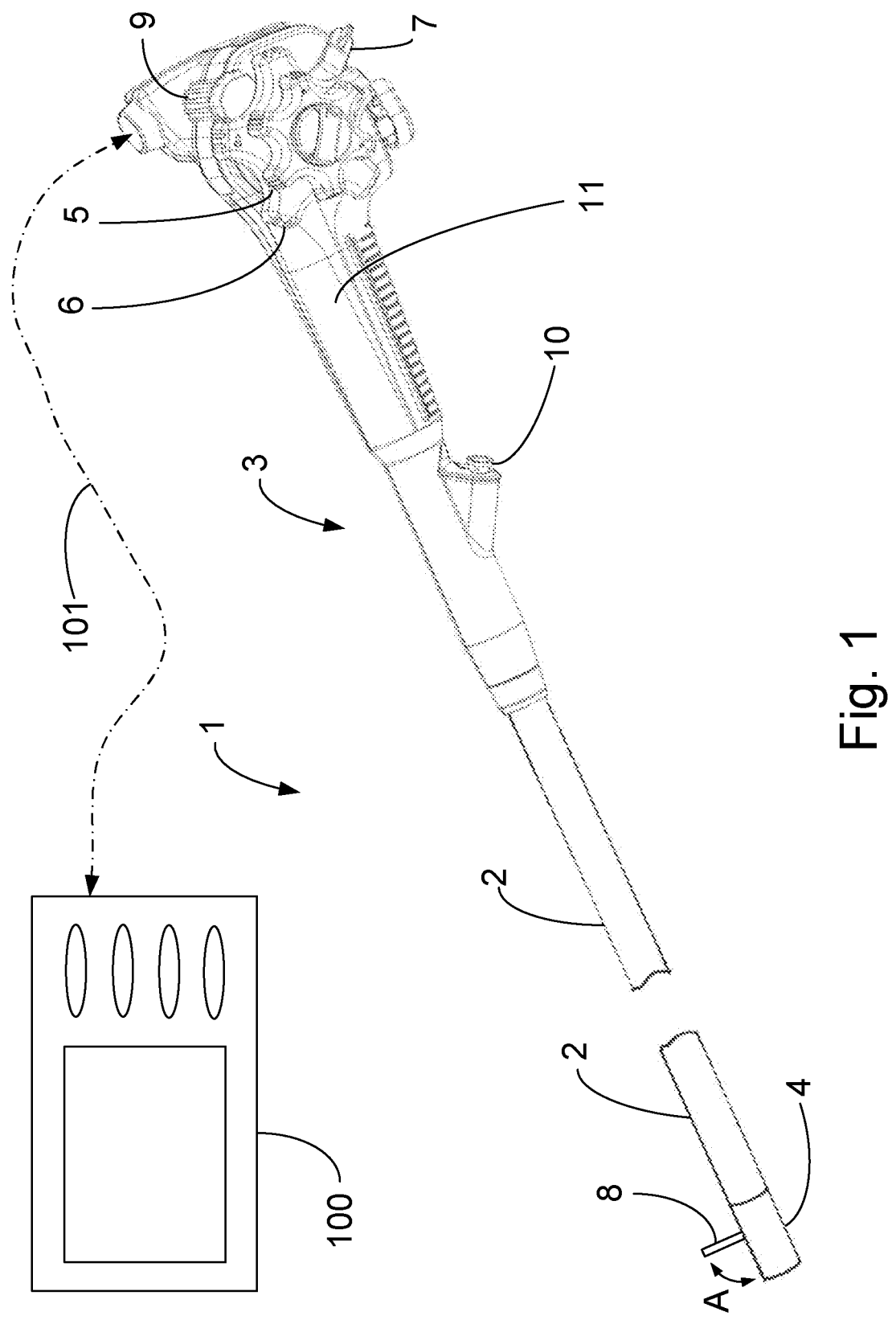
FIG. 1 schematically shows isometric view an endoscope incorporating the disclosure.

Turning first to FIG. 1, an endoscope 1 is shown. The endoscope 1 is adapted to form part of a system also comprising a display device 100 connectable to the endoscope 1 via a cable 101 or wireless communication. The illustrated endoscope is more specifically a duodenoscope. The endoscope 1 comprises an insertion tube 2 and a handle 3. At the distal end of the insertion tube 2 a bending section 4 is provided. As compared to the insertion tube 2, which is bendable to allow it to follow the bends and turns in body cavities, the bending section is highly flexible and may be actively bent in small curvatures by an operator manipulating control knobs 5, 6. A brake lever 7 allows the bending section 4 to be locked in a desired curvature.

At the bending section 4 a tool lift 8, also known as an Albarran lever, for diverting a tool inserted through the insertion tube from an entry port 10 is arranged. The tool lift 8 is essentially an arm that may be swung away from the insertion tube 2. This swinging motion is controlled by an operator using a control lever 9, which via a kinematic chain that transmits motion of the control lever 9 to the tool lift 8.

Figure 3:
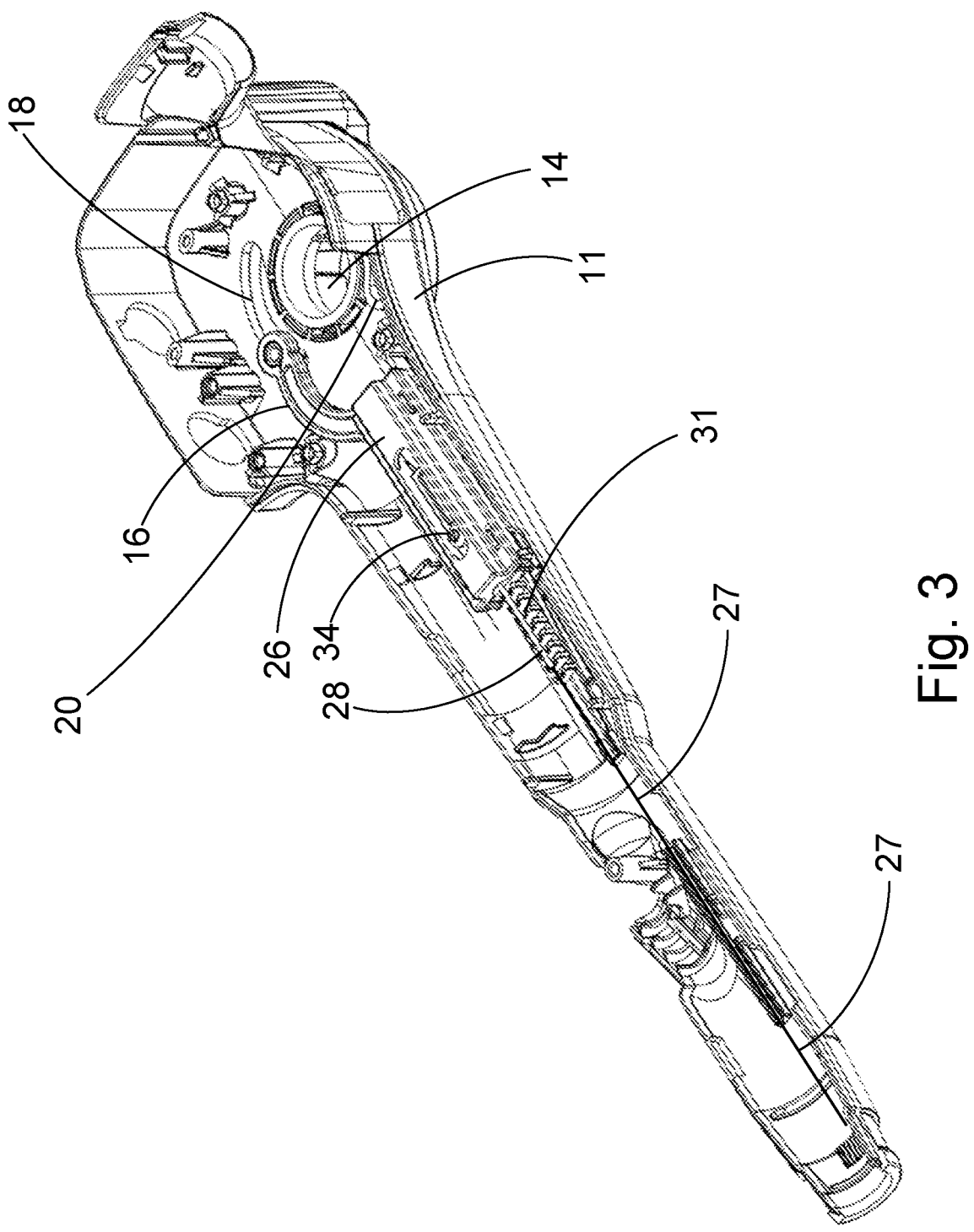
FIG. 3 shows the shell shaped-housing part of FIG. 1 with a sliding motion transfer member according to the disclosure along with other parts of the kinematic chain of an actuator mechanism of the endoscope.
Figure 4A:
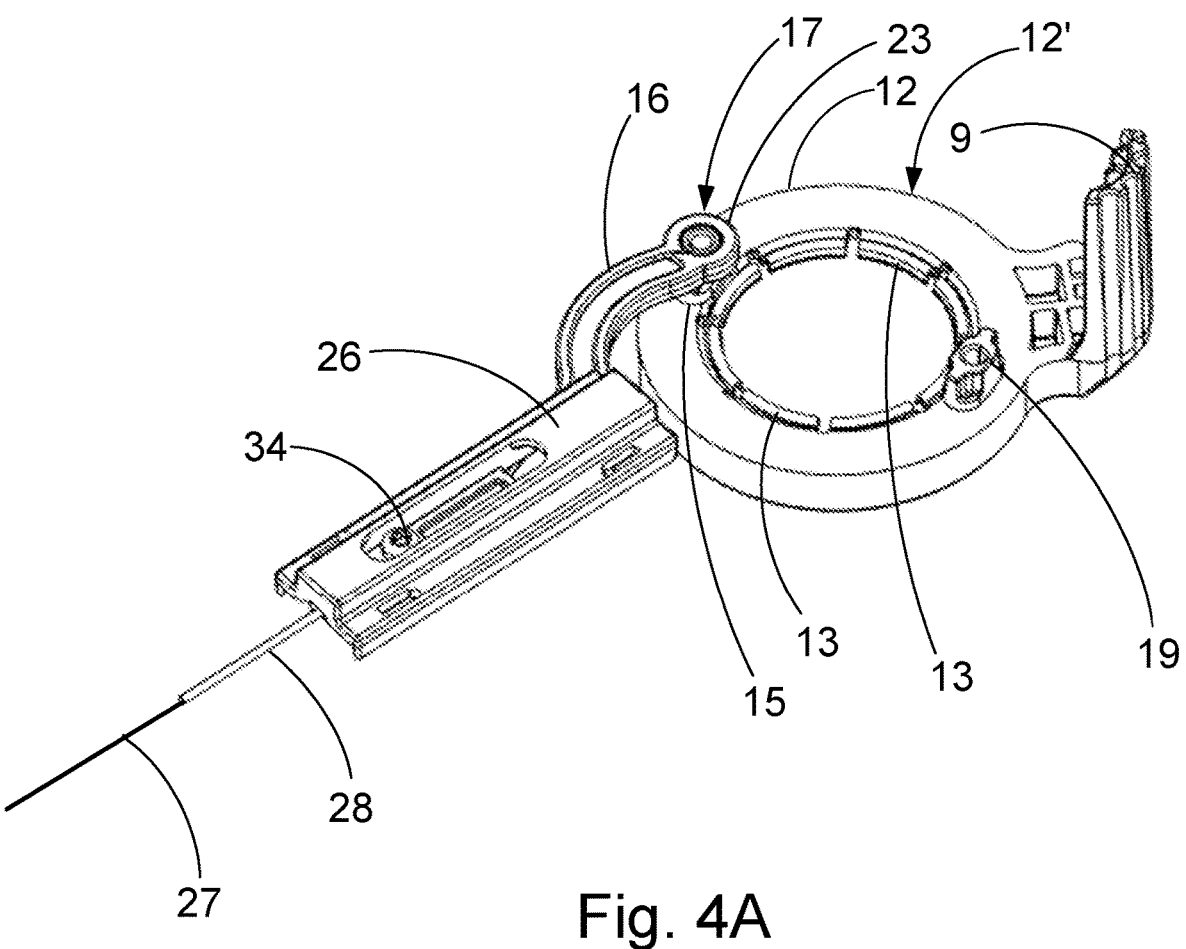
FIGS. 4A and 4B show details of the sliding motion transfer member according to the disclosure along with other parts of the kinematic chain connected to the operating member.
Figure 4B:
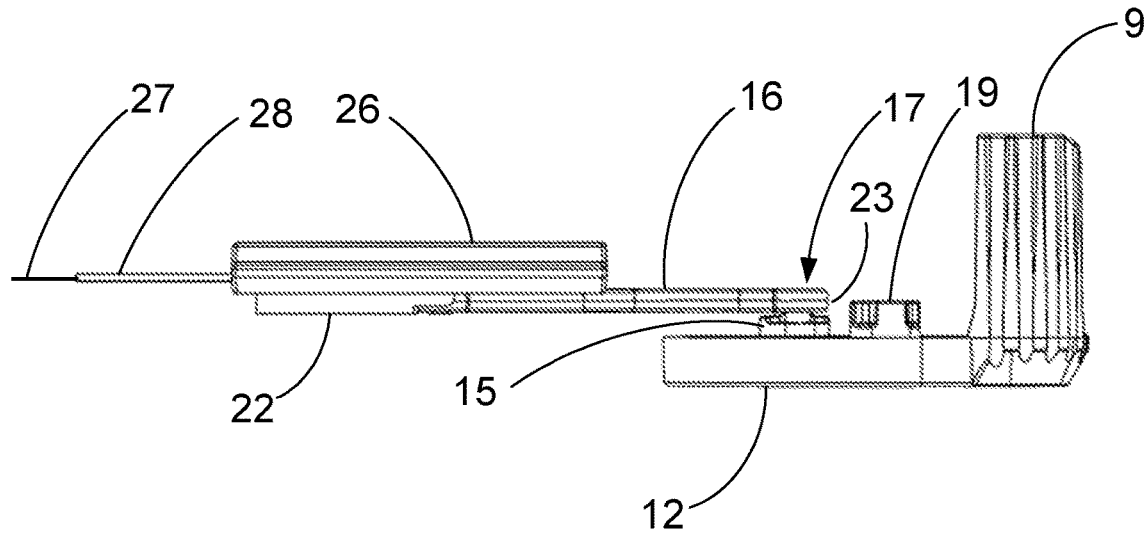

Turning now to FIGS. 4A and 4B, the relevant details of the kinematic chain according to a preferred embodiment of the disclosure will be described. As can be seen, the control lever 9 is attached to a wheel 12, preferably formed integrally therewith in a suitable manner, e.g. injection molded as a single piece, the wheel 12 and the control lever 9 forming an elevator controller 12'. The wheel 12 comprises a number of elastic friction elements 13 adapted to engage an outside cylindrical surface of a hollow shaft 14 on the handle 3, preferably formed integrally with one housing shell part 11 of the handle 3 in a suitable manner, e.g. injection molded as a single piece, cf. FIG. 2 or 3. The wheel 12 furthermore comprises a first attachment protrusion 15 to which a first end 23 of a curved rod 16 is attached to form a first hinge 17. The attachment of the curved rod 16 to the attachment protrusion 15 may be secured by a screw (not shown). Since the wheel 12 is arranged on the outside of the housing shell part 11, the attachment protrusion 15 passes through a first curved slot 18 in the housing shell part 11 to the inside of the handle 3. When the operator moves the wheel 12 by means of the control lever 9, the protrusion may move back and forth in the curved slot 18. Diametrically opposite the attachment protrusion 15 is a guiding protrusion 19 which is guided in a second curved slot 20 when the operator turns the wheel 12. The second curved slot 20 may be surrounded by upright walls so as to improve the guidance of the guiding protrusion 19 in the second curved slot 20, when the operator turns the wheel 12.

Figure 2:
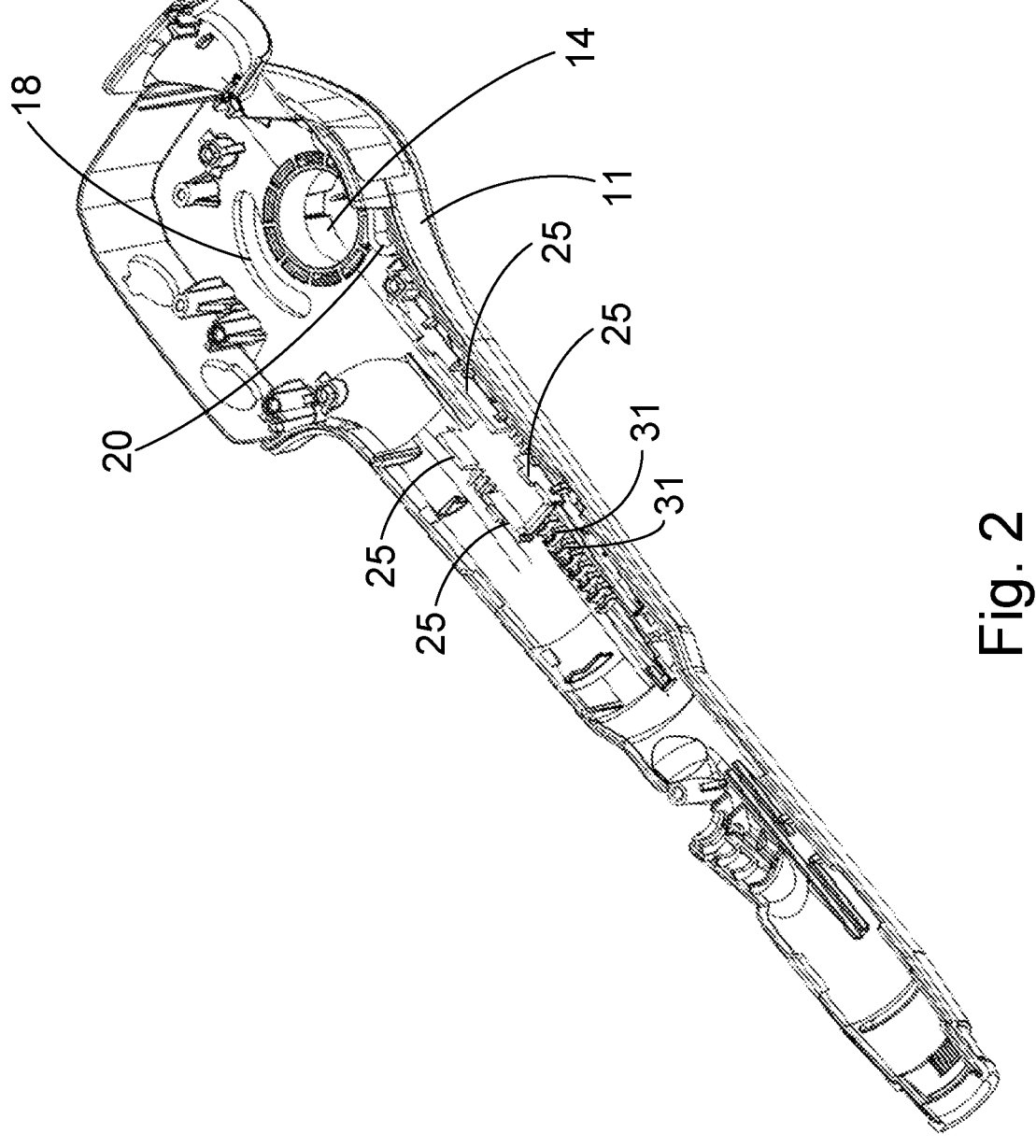
FIG. 2 shows one shell-shaped housing part of the endoscope incorporating the disclosure.
Figure 5A:
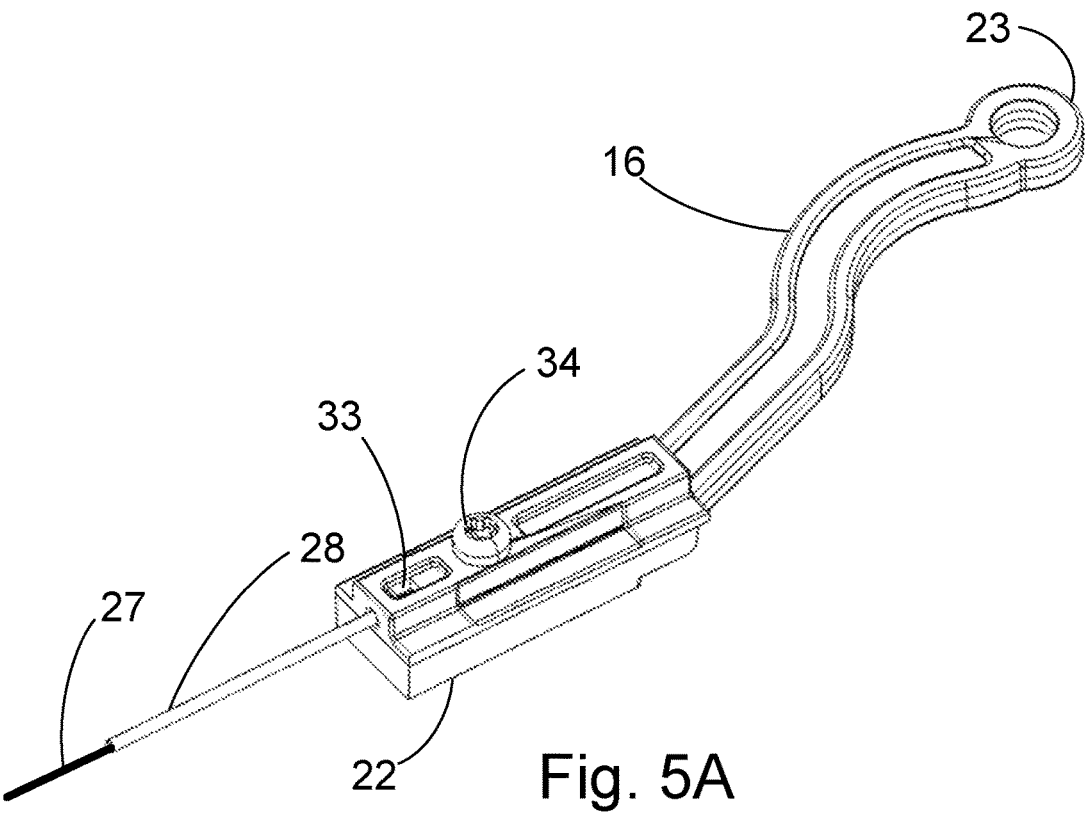
FIGS. 5A and 5B show details of the sliding motion transfer member according to the disclosure along with other parts of the kinematic chain.
Figure 5B:
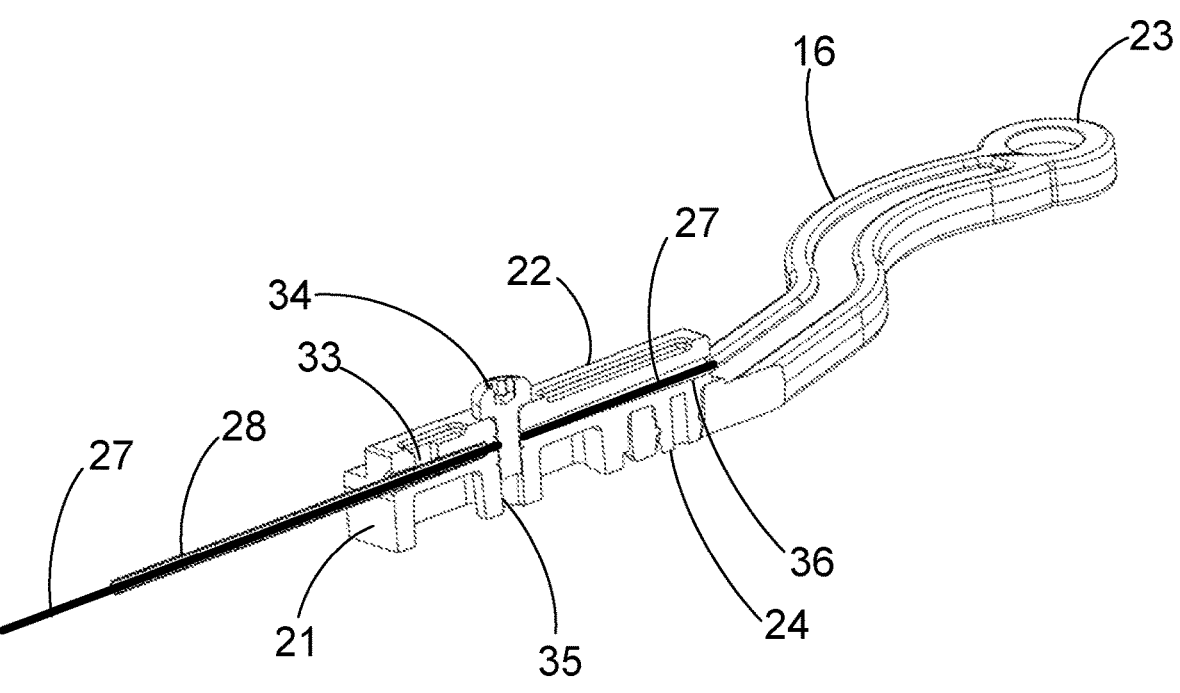

As can best be seen in FIGS. 5A and 5B, the second end of the curved rod 16 is attached to a first or proximal end of a sliding motion transfer member 22, e.g. by means of a protrusion 24 engaging a hole provided in the second end of the curved rod 16, thereby forming a second hinge. The curved rod 16 thus provides a piston rod like arrangement between the rotary wheel 12 and the sliding motion transfer member, allowing the sliding motion transfer member 22 to perform a reciprocating sliding motion with respect to the handle 3, more specifically with respect to guiding walls 25 or the like provided on the inside of the housing shell part 11. The guiding walls 25 are also preferably formed integrally with one housing shell part 11 of the handle 3, e.g.

injection molded as a single piece, cf. FIG. 2. To secure the sliding motion transfer member 22 between the guiding walls, i.e. preventing it from popping out from the location between the guiding walls 25, a lid 26 is preferably provided over the guiding walls 25. As can best be seen in FIGS. 3 and 4A, the lid may comprise an oblong hole inter alia allowing access to a mounting screw 34 in the sliding motion transfer member 22 irrespective of the current positon of the sliding motion transfer member 22.

To avoid unnecessary friction between the sliding motion transfer member 22 and the parts surrounding it on four sides, i.e. the guiding walls 25, the lid 26, and the external wall of the housing shell part 11 between the guiding walls, the sliding motion transfer member is preferably made from a low friction material, preferably a material different from the material or materials from which the guiding walls 25, the lid 26, and the housing shell part are made, one such currently preferred material is POM.

Figure 7:
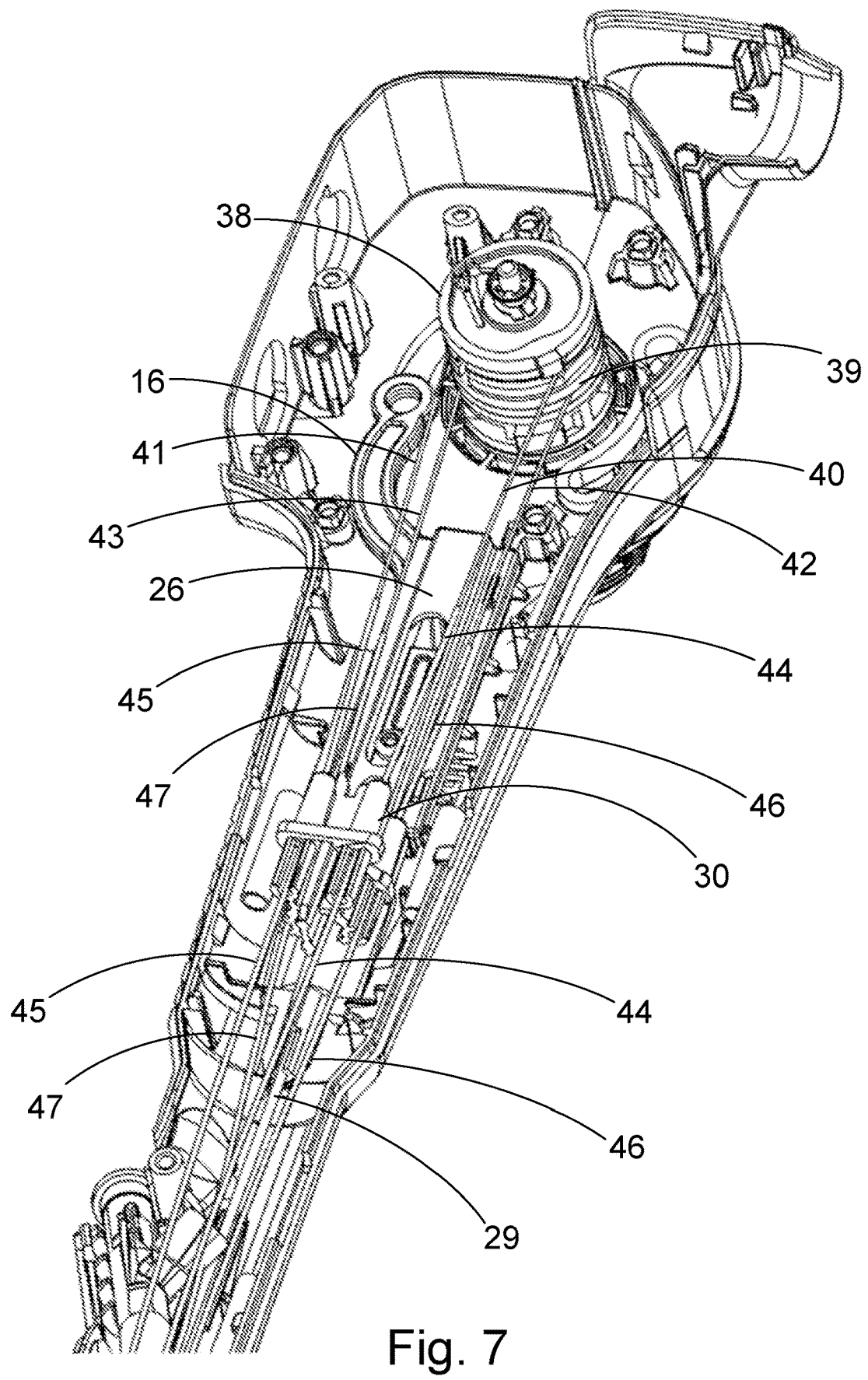
FIG. 7 shows an anchoring block in the shell-shaped housing part of the endoscope with parts of other kinematic chains.

To transmit the reciprocating motion of the sliding motion transfer member 22 through the insertion tube 2 of the endoscope 1 to the tool lift 8 at the distal end of the endoscope 1, the endoscope comprises an elongate motion transmission member 27, e.g. single strand steel wire, such as a piano wire, acting as a push-rod. In the insertion tube 2 the elongate motion transmission member 27 is preferably guided in a sheath 29 or mantle preventing it from buckling under compression. As can be seen in FIG. 7, the proximal end of the sheath 29 is terminated in an anchoring block 30 in the handle 3. The anchoring block 30 will be discussed further below.

To prevent the proximal part of the elongate motion transmission member 27, between the sliding motion transfer member 22 and the guiding sheath, from buckling, the proximal part of the sliding motion transfer member 22 is supported by an outer rigid tubular member 28, which in turn is supported by a row of trestles 31. The outer rigid tubular member 28 is preferably a short length of steel tube. As can be seen from FIG. 5B in conjunction with FIGS. 6B and 6C, the outer rigid tubular member 28 is mounted in a first, slightly conical bore 32 in the distal end 21 of the motion transfer member 22. It is preferably secured in the mounting position by means of an adhesive poured into the bore during assembly of the endoscope, e.g. through an inlet 33 provided in the motion transfer member 22 for that purpose. Although the adhesive will not adhere that well to the low friction POM from which the motion transfer member 22 is made it suffices, as the rigid tubular member 28 really only needs to be held in place in the motion transfer member 22 and ideally no external forces try to separate the two. Furthermore, if as preferred the outer rigid tubular member 28 is made of steel, the adhesive will adhere properly to the steel and together with the remaining adhesive set in the inlet 33 form a mechanical form locking, or adhesive anchor, between the adhesive and the motion transfer member 22.

For the elongate motion transmission member 27, the secure mounting in thereof in the motion transfer member 22 is much more difficult, because it needs to transmit forces when acting as a push-rod, but in particular when pulling back there is a risk of large forces occurring, e.g. if the tool lift 8 were in some way to be blocked from motion in an extended position and prevented from retraction. The elongate motion transmission member 27 is therefore preferably secured in dual ways with respect to the motion transfer member 22.

The first way is using a screw 34, preferably and conventionally made of steel, screwed into a second bore 35 arranged in a transversal direction with respect to the longitudinal direction of the motion transfer member 22, e.g. perpendicular to the axis of the first bore 32 and a third, preferably conical bore 36. The bore 32 and the third bore 36 form a contiguous passage 22a into which the elongate motion transmission member 27 is inserted during manufacture. When, during manufacture, the elongate motion transmission member 27 has been inserted in place in the in the first and third bores 32, 36 the screw 34 will, when screwed into the second bore 35, deform the elongate motion transmission member 27 so that it will pass one or the other way around the screw 34 or be pushed down into the bore 35 or even a combination of both, thereby securing high friction against the screw 34 to hold the elongate motion transmission member 27 in position in the motion transfer member 22 against pushing or pulling forces.

Figures 6A, 6B, 6C:
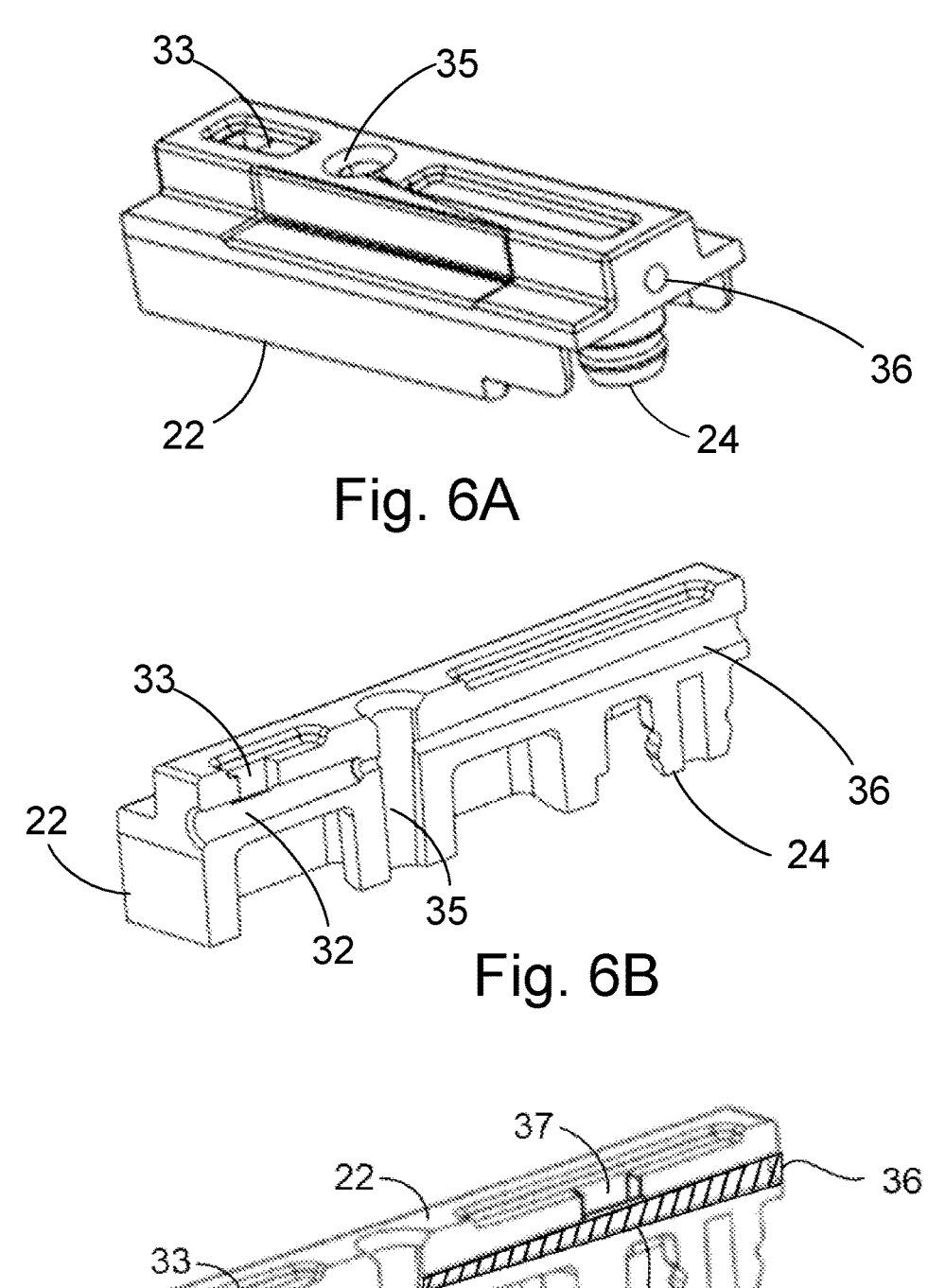
FIG. 6A shows an isometric view of the motion transfer member
FIG. 6B shows a cross-section of the sliding motion transfer member.
FIG. 6C shows a cross-section of an alternative embodiment of the sliding motion transfer member.

The second way is using a form locking glue plug 32a, 36a of the adhesive, or adhesive anchor, in a manner similar to the rigid tubular member 28. More specifically, adhesive poured into the conical third bore during manufacture of the endoscope 1 will adhere to the elongate motion transmission member 27 and when it sets form a conical glue plug 36a around the proximal end of the elongate motion transmission member 27. The conical plug formed on the end of the elongate motion transmission member 27 will prevent the elongate motion transmission member 27 from being drawn out of the motion transfer member 22 by excessive pulling forces by the operator that could occur should the tool lift 8 lever be blocked in the extended position. Because this is dependent on the matching conical forms of the glue plug and the bore the possible lack of adherence of the adhesive to the POM or other material of the motion transfer member 22 becomes less of an issue. As depicted in FIG. 6C, a glue inlet 37 is connected to the third bore 36. This facilitates the pouring of the adhesive during manufacturing, and when the adhesive has set gives additional form locking the glue plug 36a with respect to the motion transfer member 22 inter alia improving further the resistance of the assembly to pushing forces.

As mentioned above, the force transmission via the kinematic chain from the control lever 9 via the elongate motion transmission member 27 to the tool lift 8 passes through an anchoring block 30 into the sheath 29. The anchoring block 30, however, serves as an anchoring block 30 not only for this kinematic chain, by also for others kinematic chains, in particular the kinematic chains to the bending section 4. These other kinematic chains, however, are kinematically independent of the kinematic chain to the tool lift 8 and consequently the anchoring block 30 and the advantages thereof for the bending section 4 may be employed independently of whether the endoscope comprise a tool lift 8 or not.

As for these other kinematic chains, a first pulley 38 and a second pulley 39 inside the handle 3 are attached to respective control knobs 5, 6 on the outside of the handle 3 via concentric axles (not visible) through the hollow shaft 14. A first pull wire 40 and a second pull wire 41 are attached to more or less diametrically opposite sides of the first pulley 38. Likewise, a third pull wire 42 and a fourth pull wire 43 is attached to more or less diametrically opposite sides of the second pulley 39.

The pull wires 40, 41, 42, 43 are connected to the bending section 4 in a manner per se known, so that pulling one of them (and thereby slacking the opposite one, will control will control the bending of the bending section 4 in a given plane, e.g. left-right for the first pulley 38 and up-down for the second pulley 39.

To ensure proper transmission of pulling force to the bending section 4 each of the pull wires is arranged as part of a Bowden cable. Accordingly, they are surrounded by respective sleeves 44, 45, 46, 47 most of the way to the bending section. The sleeves are preferably tightly wound steel coils. However, to function as a Bowden cable the proximal ends of the respective sleeve need to be anchored in a fixed location with respect to the pulleys i.e. with respect to the handle housing shell 11 on which the first and second pulleys 38, 39 are mounted.

The anchoring block 30 inter alia serves this purpose. Accordingly, the anchoring block 30 is adhered to the inside of the shell-shaped handle housing part 11. This is preferably done using a UV setting resin as the glue, and the anchoring block 30 is in that case made of a transparent polymer material.

As will be understood from FIG. 7 the anchoring block comprises four through bores adapted to accommodate a respective sleeve. As can better be seen in FIG. 8 where most other parts than the shell-shaped handle housing 11 and the anchoring block 30 have been removed, one end of each though bore comprises an open slit 48, 49, 50. The bores and the open slits 48, 49, 50 are arranged in pairs at two levels in the anchoring block 30 that is to say the axes of the open slits 48 and 49 (and the bores) lie in the same plane PU defining an upper level and likewise the axes of the open slits 50 and 51 lie in another plane defining a lower level PL as indicated with dashed lines in FIG. 9. Upper and lower are in this context to be understood in accordance with the drawing, and as reflecting the fact that during assembly the shell-shaped handle housing part 11 will normally be lying on a table or held in a similar manner with the opening facing upward for easy access.

To support the easy access during assembly, the spacing between the open slits 48 and 49 in the upper level is less than the spacing between the open slits 50 and 51 in the lower level i.e. so that upper parts of the anchoring block 30 do not unnecessarily restrict access to the lower parts when, during manufacture, adhesive has to poured into the open slits 48, 49, 50, 51 to secure the sleeves in the bores in the anchoring block 30. To further facilitate this access, the openings in the open slits 50 and 51 in the lower level face slightly sideways away from the anchoring block 30, so that adhesive can be poured in from the side. That is to say where the openings of the open slits 48, 49 face upwards perpendicular to the upper level plane PU defined between them and indicated by the interrupted lines, whereas the opening of the open slits 50 and 51 at the lower level PL, face outwardly at opposite angles to the plane defined between them as also indicated with dashed lines. Pouring adhesive into the open slits 48, 49, 50, 51 from the directions indicated by the respective arrows of those reference numerals in FIG. 9 for securing the sleeves 44, 45, 46, 47 in the anchoring block 30 is thus facilitated even though the anchoring block 30 has already been adhered to the bottom of the shell-shaped handle housing part 11 in an earlier stage of the assembling process. At the distalmost end of the anchoring block 30 the anchoring block comprises a further open slit open slit 52, in communication with a fifth through bore.

Figure 8:
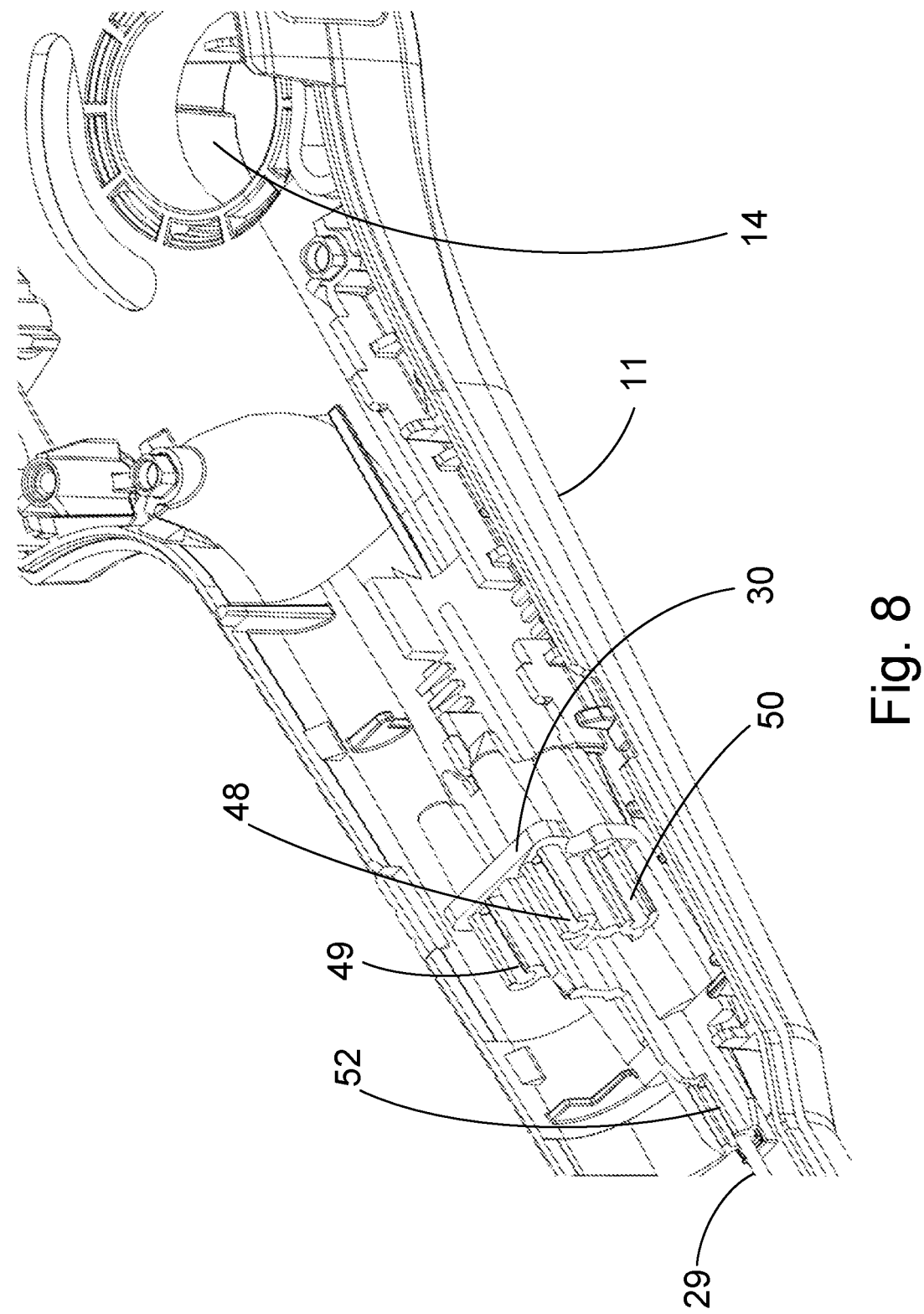
FIG. 8 shows a detailed view of the anchoring block with in the shell-shaped housing part.
Figure 9:
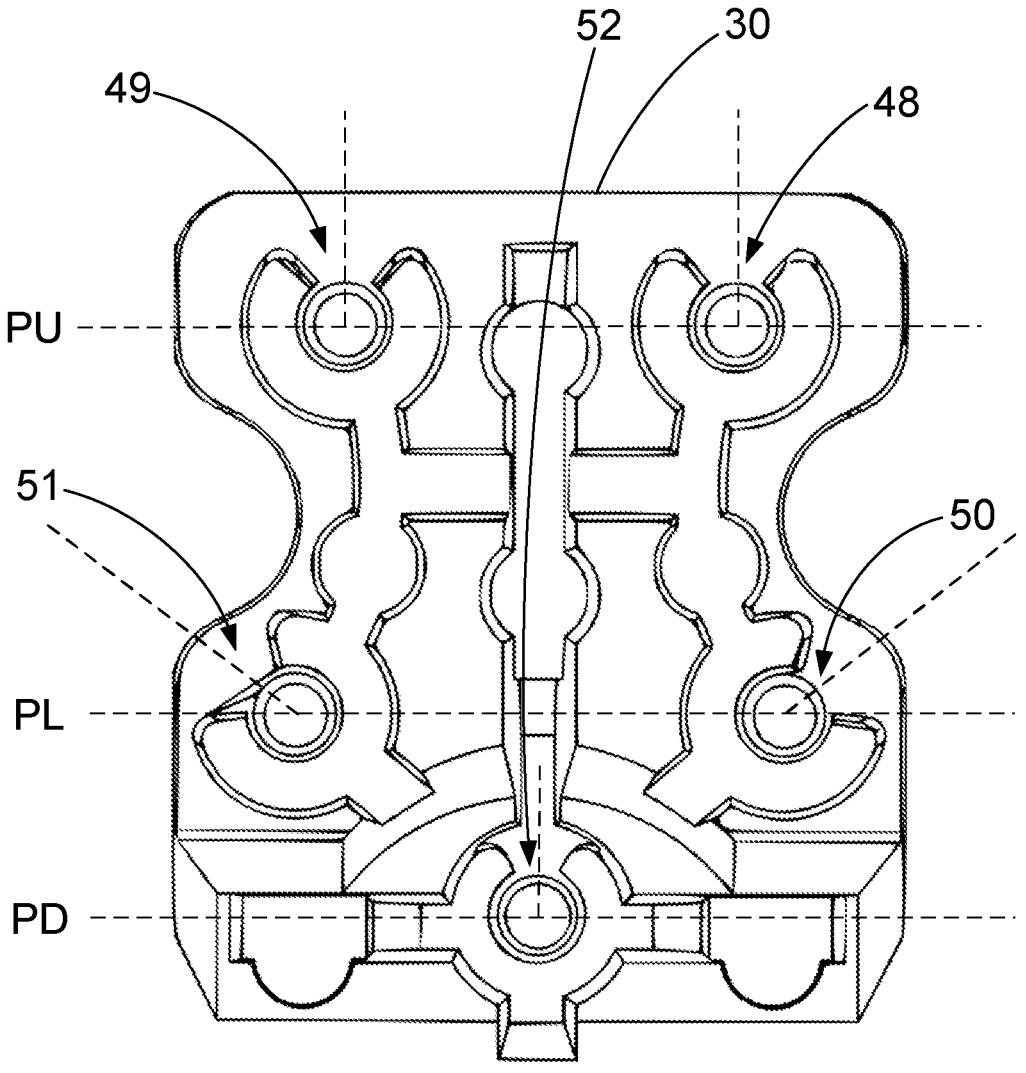
FIG. 9 shows an end view of the anchoring block.

As can be seen from FIGS. 8 and 9, this further open 52 slit is located more distal than the four other bores in an even lower and plane PD, than the planed PU and PL. This further open slit 52 is adapted to receive the proximal end of the sheath 29. Similar to the other open slits 48, 49 the further open slit 52 is easily accessible form above and therefor open in the vertical direction to allow adhesive to be poured into the further open slit 52 in order to set and secure the position of the proximal end of the sheath 29 with respect to the anchoring block 30. The entire anchoring block 30 is preferably integrally moulded in one single piece. Moreover, as already mentioned above the anchoring block 30 may be made of a transparent polymer material, therefore also allowing the use of UV curing adhesive or resin as glue in the open slits 48, 49, 50, 51, 52, which may then be irradiated from all sides through the anchoring block.

In other aspects the disclosure also comprises:

A. An anchoring block for multiple kinematic chains, said anchoring block comprising a number of through bores adapted to receive sleeves of respective Bowden cables, wherein at least one of said through bores is in communication with an open slit.

B. An anchoring block according to A, wherein the open four open slits are arranged in two pairs at different levels of said anchoring block.

C. An anchoring according to B wherein the open slits in one level are at an angle to the open slits in the other level.

D. An anchoring block according to B or C, wherein a fifth open slit is arranged at a third level.

E. An anchoring block according to any one of B through D, wherein the open slits in one level are arrange with an angle between them, i.e. not in parallel.

F. An anchoring block, according to any one of A through E wherein the anchoring block is manufactured as an integrally moulded single-piece item.

G. An anchoring block according to any one of A through F, wherein the anchoring block is manufactured from a transparent material, preferably a transparent polymer material.

We claim:

1. An endoscope comprising:
a handle comprising a hollow shaft;
an elongate motion transmission member extending from the handle and comprising a proximal section;
an elevator controller comprising a wheel, a control lever, and friction elements, the wheel and the friction elements comprising a one-piece part including a hole, the hollow shaft protruding through the hole and being engaged by the friction elements;
a curved rod pivotally connected to the wheel;
a sliding motion transfer member pivotally connected to the curved rod and configured to translate in response to a motion activation input applied at the control lever, said sliding motion transfer member comprising a longitudinal passage, the longitudinal passage including a first bore and a third bore proximal of the first bore, the proximal section of said elongate motion transmission member being adhesively secured to said sliding motion transfer member at the first bore and/or at the third bore.

2. The endoscope of claim 1, wherein the sliding motion transfer member comprises a second bore traversing the longitudinal passage between the first bore and the third bore.

3. The endoscope of claim 2, wherein the third bore comprises a frustoconical shape in which a proximal opening of the frustoconical shape is larger than a distal opening thereof, wherein the sliding motion transfer member comprises an adhesive inlet passage in fluid communication with respect to said third bore, the endoscope further comprising an adhesive anchor and a mounting screw, the adhesive anchor comprising a frustoconical plug adhesively secured to the proximal section at the third bore and extending into the adhesive inlet passage, and the mounting screw being received in the second bore and deforming the proximal section.

4. The endoscope of claim 1, the endoscope further comprising a rigid tube inserted in the first bore, wherein the proximal section of the elongate motion transmission member extends through, and is supported by, the rigid tube, and wherein the third bore comprises a frustoconical shape in which a proximal opening of the frustoconical shape is larger than a distal opening thereof.

5. The endoscope of claim 4, wherein the sliding motion transfer member comprises an adhesive inlet passage in fluid communication with respect to said third bore, the endoscope further comprising an adhesive anchor comprised of a cured adhesive being adhesively secured to the elongate motion transmission member at the third bore and extending into the adhesive inlet passage.

6. The endoscope of claim 5, wherein the third bore has a varying cross-sectional area.

7. The endoscope of claim 6, wherein the cross-sectional area increases in a distal to proximal direction.

8. The endoscope of claim 5, wherein the adhesive anchor comprises a frustoconical plug.

9. The endoscope of claim 2, the endoscope further comprising a mounting screw received by the second bore in a manner allowing said mounting screw to engage and deform said proximal section of said elongate motion transmission member to further secure the proximal section to the elongate motion transmission member.

10. The endoscope of claim 9, wherein the handle comprises a housing shell part having an internal surface facing an interior of the handle, wherein the housing shell part comprises a one-piece part including guiding walls configured to retain in a sliding manner the sliding motion transfer member.

11. The endoscope of claim 10, the endoscope further comprising a lid attached to the guiding walls and further securing the sliding motion transfer member, wherein the lid comprises an oblong hole configured to receive the mounting screw.

12. The endoscope of claim 11, wherein the first bore is frustoconical.

13. The endoscope of claim 1, wherein the sliding motion transfer member comprises a first adhesive inlet passage in fluid communication with respect to said first bore and a second adhesive inlet passage in fluid communication with respect to said third bore, the endoscope further comprising a first adhesive anchor and a second adhesive anchor, the second adhesive anchor adhesively secured to the proximal section at the third bore and extending into the second adhesive inlet passage.

14. The endoscope of claim 13, wherein the sliding motion transfer member comprises a second bore traversing the longitudinal passage between the first bore and the third bore, and wherein the second passage is configured to receive a mounting screw in a manner allowing said mounting screw to engage and deform said proximal section of said elongate motion transmission member to further secure the proximal section to the elongate motion transmission member.

15. The endoscope of claim 1, wherein the sliding motion transfer member comprises a first adhesive inlet passage in fluid communication with respect to said first bore and a second adhesive inlet passage in fluid communication with respect to said third bore, the endoscope further comprising a first adhesive anchor and a second adhesive anchor, the first adhesive anchor extending into the first adhesive inlet passage, and the second adhesive anchor adhesively secured to the proximal section at the third bore and extending into the second adhesive inlet passage, wherein the sliding motion transfer member comprises a second bore traversing the longitudinal passage between the first bore and the third bore, and wherein the second passage is configured to receive a mounting screw in a manner allowing said mounting screw to engage and deform said proximal section of said elongate motion transmission member to further secure the proximal section to the elongate motion transmission member.

16. The endoscope of claim 1, wherein the elevator controller comprises an attachment protrusion and a guiding protrusion, wherein the handle comprises a first curved slot and a second curved slot, wherein the wheel is positioned outside the handle, wherein the attachment protrusion and the guiding protrusion are connected to the wheel and extend through, respectively, the first curved slot and the second curved slot, and wherein the attachment protrusion is connected to the curved rod to pivotally connect the curved rod to the wheel.

17. A system comprising:
the endoscope of claim 1; and
a display unit connectable to said endoscope.

18. The endoscope of claim 1, wherein the handle comprises a housing shell part having an internal surface facing an interior of the handle, wherein the housing shell part comprises a one-piece part including guiding walls configured to retain in a sliding manner the sliding motion transfer member.

19. The endoscope of claim 1, wherein the third bore comprises a frustoconical shape in which a proximal opening of the frustoconical shape is larger than a distal opening thereof, wherein the sliding motion transfer member comprises an adhesive inlet passage in fluid communication with the third bore, the endoscope further comprising an adhesive anchor comprising a frustoconical plug adhesively secured to the proximal section at the third bore and extending into the adhesive inlet passage.

20. The endoscope of claim 1, wherein the friction elements comprise curved surfaces biased into frictional engagement with the hollow shaft.

* * * * *